(12) United States Patent
Toddes et al.

(10) Patent No.: US 9,615,801 B2
(45) Date of Patent: Apr. 11, 2017

(54) ANIMAL HOLDER FOR PERFORMING NEUROIMAGING

(71) Applicant: Animal Imaging Research, LLC, Westminster, MA (US)

(72) Inventors: Steven Toddes, Westminster, MA (US); Craig Ferris, Westminster, MA (US)

(73) Assignee: ANIMAL IMAGING RESEARCH, LLC, Westminster, MA (US)

( * ) Notice: Subject to any disclaimer, the term of this patent is extended or adjusted under 35 U.S.C. 154(b) by 628 days.

(21) Appl. No.: 13/648,518

(22) Filed: Oct. 10, 2012

(65) Prior Publication Data

US 2014/0100444 A1    Apr. 10, 2014

(51) Int. Cl.

| | | |
|---|---|---|
| *A61B 5/05* | (2006.01) | |
| *A61B 6/04* | (2006.01) | |
| *A61B 5/055* | (2006.01) | |
| *A61B 6/03* | (2006.01) | |
| *A61B 5/00* | (2006.01) | |
| *A61B 6/00* | (2006.01) | |

(52) U.S. Cl.
CPC .......... *A61B 6/0421* (2013.01); *A61B 5/0555* (2013.01); *A61B 5/702* (2013.01); *A61B 6/032* (2013.01); *A61B 6/037* (2013.01); *A61B 6/0428* (2013.01); *A61B 6/547* (2013.01); *A61B 5/0042* (2013.01); *A61B 6/508* (2013.01)

(58) Field of Classification Search
CPC ........... A61B 6/0421; A61B 5/05; A61B 6/00
See application file for complete search history.

(56) References Cited

U.S. PATENT DOCUMENTS

| | | | |
|---|---|---|---|
| 2001/0053878 A1* | 12/2001 | Ferris et al. ................... | 600/415 |
| 2007/0191706 A1* | 8/2007 | Calderon et al. ............. | 600/415 |
| 2010/0188087 A1* | 7/2010 | Tammer ............... | A61B 5/0555 |
| | | | 324/321 |
| 2010/0315085 A1* | 12/2010 | Brown et al. .................. | 324/309 |
| 2011/0083614 A1* | 4/2011 | Chen et al. .................... | 119/729 |

\* cited by examiner

*Primary Examiner* — Joel Lamprecht

(74) *Attorney, Agent, or Firm* — Leason Ellis LLP

(57) ABSTRACT

An animal holder for use with an imaging device includes a body tube for receiving a first body portion of the animal. The animal holder also includes a head immobilization mechanism disposed adjacent one end of the body tube for receiving a head of the animal. The head immobilization mechanism includes opposing first and second flexible fingers that have free ends configured to contact and immobilize the head of the animal when the fingers are moved to a compressed position.

12 Claims, 8 Drawing Sheets

ANIMAL HOLDER FOR PERFORMING NEUROIMAGING

TECHNICAL FIELD

The present invention is generally directed to magnetic resonance imaging and more particularly, to a holder for a small animal (e.g., a rodent, such as a mouse) for holding a head of an animal in a stationary position as imaging (e.g., magnetic resonance imaging (e.g., fMRI)) is performed when the animal is either in a conscious state or an unconscious (i.e., anesthetized) state.

BACKGROUND

Human studies utilizing MRI have advanced our understanding of the regional and functional interplay between populations of neurons serving sensory, integrative and motor functions. Changes in neuronal activity are accompanied by specific changes in hemodynamics such as cerebral blood flow, cerebral blood volume, and blood oxygenation. Functional MRI has been used to detect these changes in response to visual stimulation, somatosensory activation, motor tasks, and emotional and cognitive activity.

Braining imaging in animals using SPECT, PET and MR are common practices in academia and the biotechnology and pharmaceutical industries. Key to any brain imaging study is: 1) securing the head to prevent motion artifact caused by movement and 2) minimizing the discomfort to the animals. At present, head immobilization is achieved through surgically implanted head posts that can be anchored to the hardware in the imaging equipment or by ear bars and skull pins compressed against the head originating from various head support structures anchored to the imaging equipment. Head posts are invasive, while ear bars and skull pins are painful and require the application of local anesthetics to the area of contact to minimize discomfort. These problems are motion and pain reduction are exacerbated in awake animal imaging, which represents a practice that is supplanting the use of anesthetics when imaging the brain.

Thus, there is a need for an animal holder that provides an alternative means for head immobilization which overcomes the disadvantages of the conventional techniques mentioned above.

SUMMARY

In accordance with the present invention, an animal holder for use with an imaging device includes a body tube for receiving a first body portion of the animal. The animal holder also includes a head immobilization mechanism disposed adjacent one end of the body tube for receiving a head of the animal. The head immobilization mechanism includes opposing first and second flexible fingers that have free ends configured to contact the head of the animal. The first and second flexible fingers move between first and second positions, wherein in the first position, at which the first and second fingers are at rest, the first and second fingers extend beyond an outer side wall of the body tube and define a maximum width of the holder, whereas in the second position, the first and second fingers are in a inwardly flexed position in which the width of the holder at a location of the free ends of the first and second fingers is substantially the same as the width of the body tube. In the inwardly flexed position, the first and second fingers are configured to contact and immobilize the head of the animal.

BRIEF DESCRIPTION OF THE DRAWING FIGURES

DETAILED DESCRIPTION OF CERTAIN EMBODIMENTS

Figure 1:
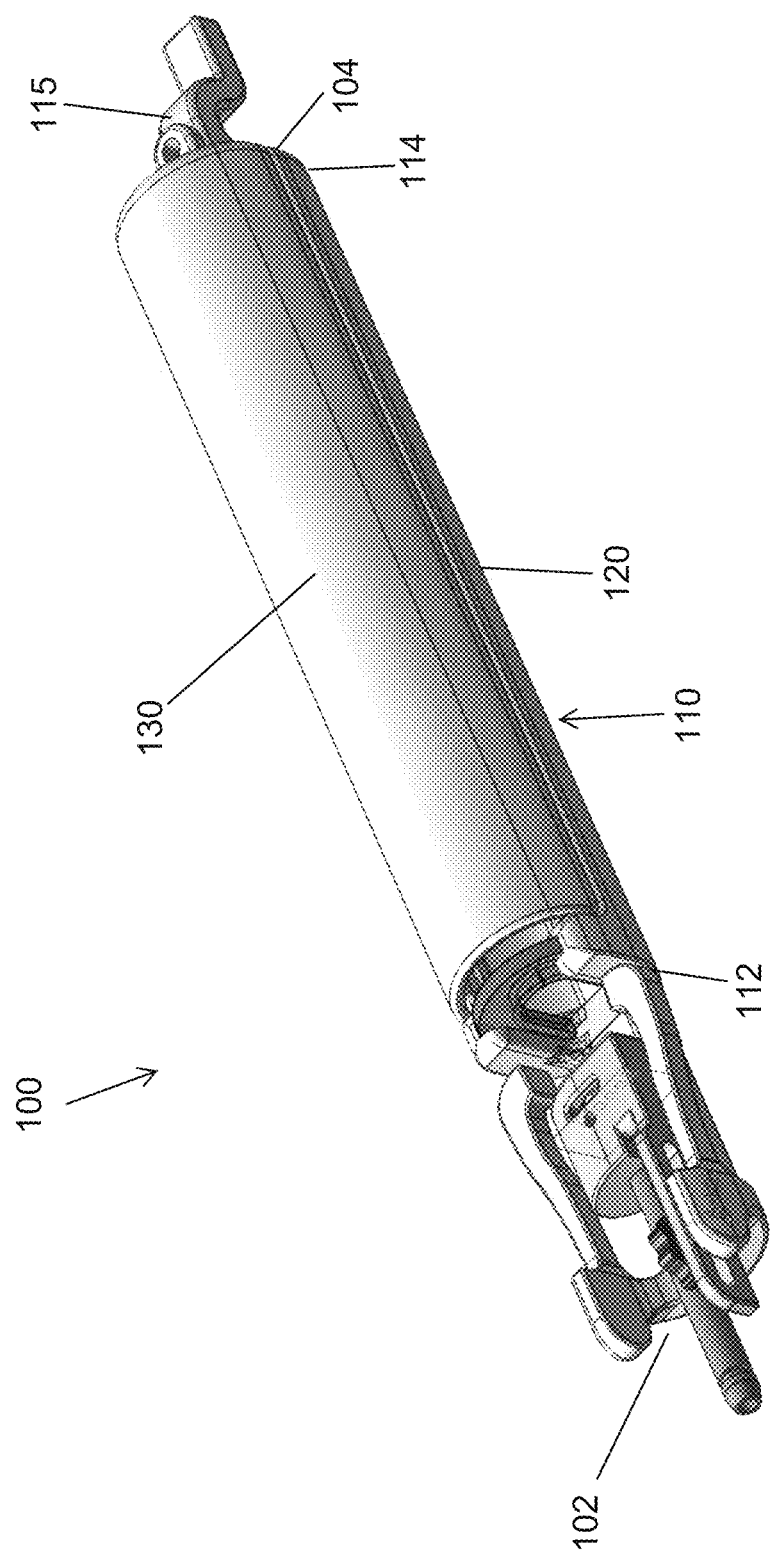
FIG. 1 is a side and top perspective view of an animal holder in accordance with one embodiment of the present invention.
Figure 2:
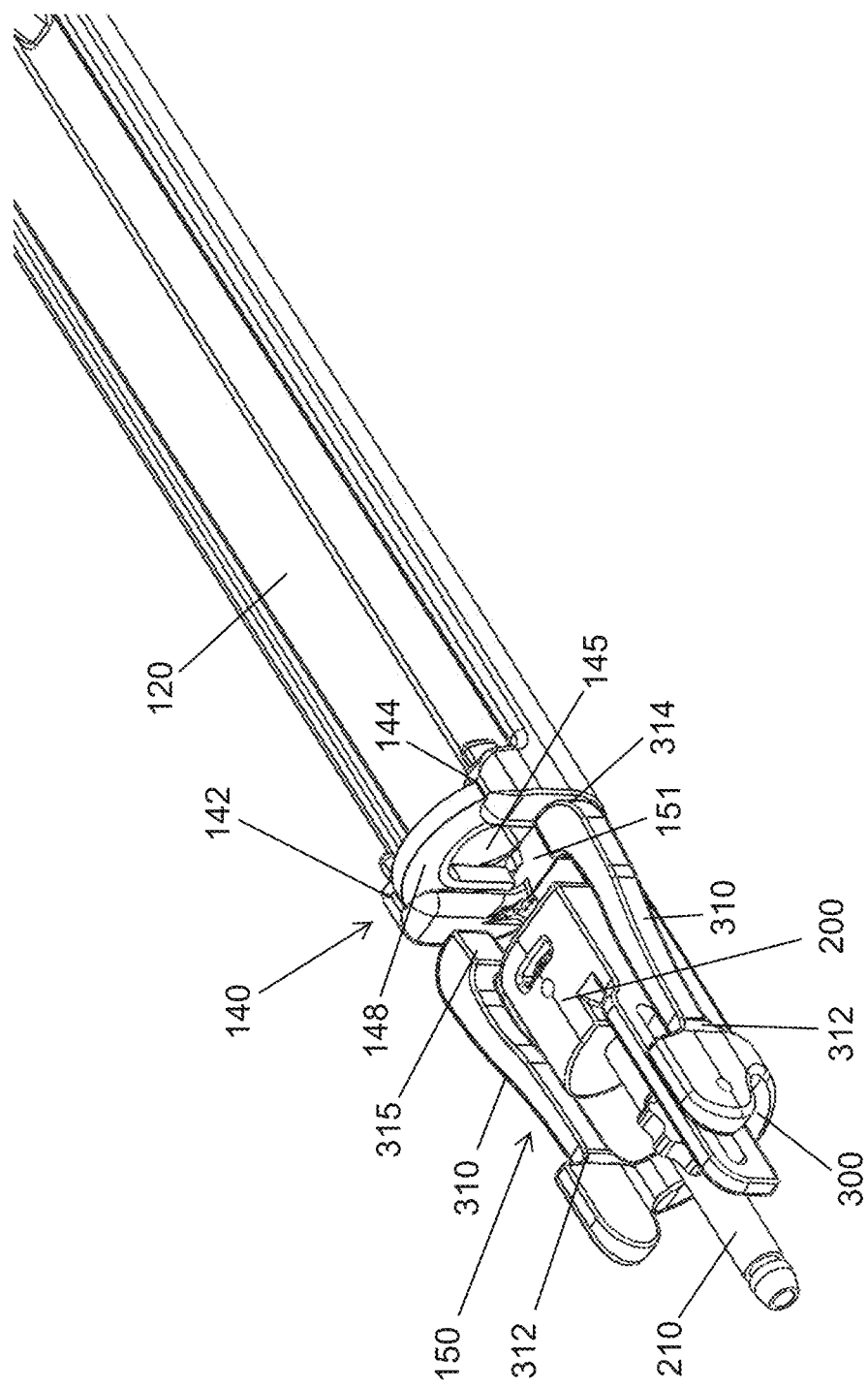
FIG. 2 is an enlarged partial side and top perspective view of the animal holder of FIG. 1 with a main cover thereof shown removed therefrom and compressible fingers of the animal holder being shown in rest (extended) positions.
Figure 3:
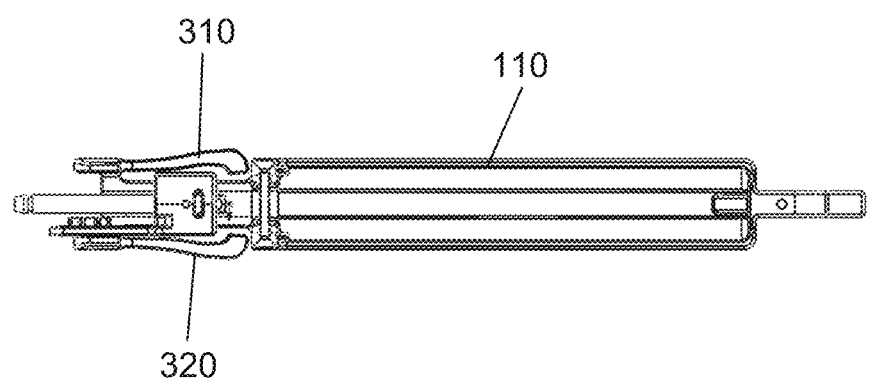
FIG. 3 is a top plan view of the animal holder of FIG. 2.
Figure 6:
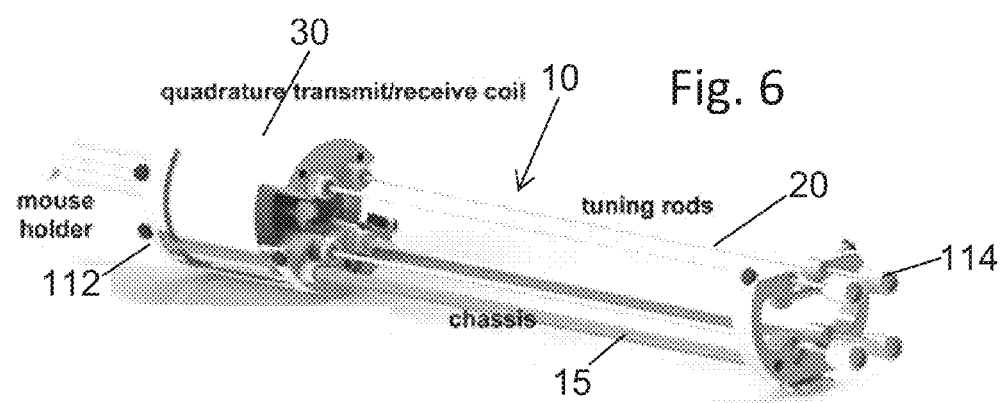
FIG. 6 illustrates the animal holder of FIG. 1 in an operative position in which the animal holder is fully inserted into a coil of an imaging device.
Figure 7:
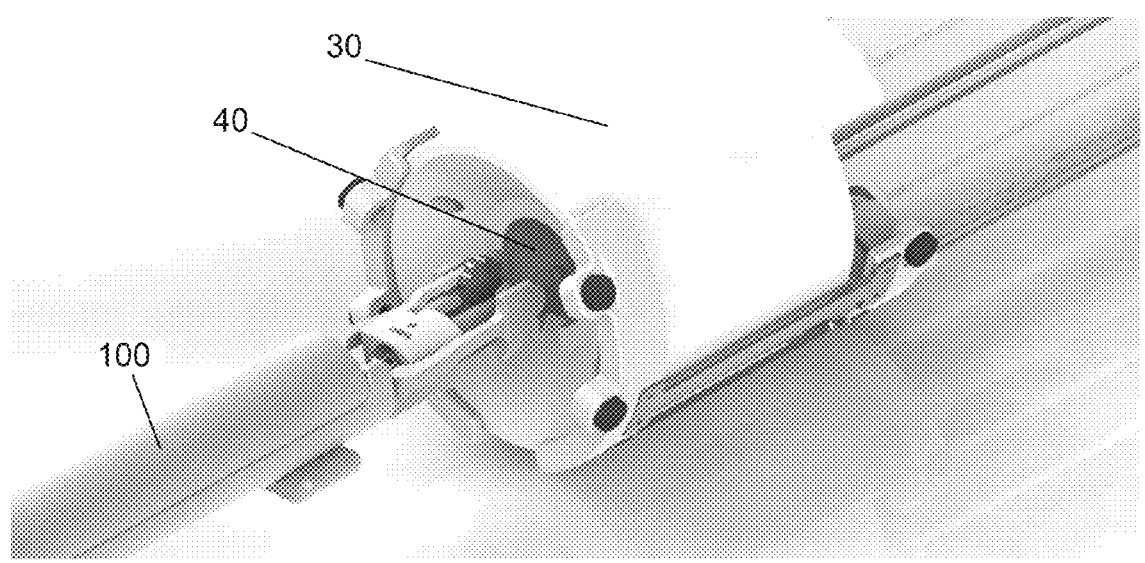
FIG. 7 illustrates the animal holder of FIG. 1 spaced from the imaging device prior to insertion into a receiving opening formed in the imaging device.

FIGS. 6 and 7 show one application of an animal holder 100 (FIG. 1) in accordance with the present invention and more specifically, FIGS. 6 and 7 show the animal holder 100 in an operative position and fully inserted into and mated with an imaging device 10. The imaging device 10 can be any number of different conventional imaging devices including but not limited to SPECT, PET and MR devices.

In the illustrated embodiment, the imaging device 10 is in the form of an MR imaging device that includes conventional components including a chassis 15 that has a first end 12 and an opposing second end 14. The device 10 also includes tuning rods 20 that are positioned above the chassis 15 as shown. At the first end 12 of the device 10, a coil assembly 30 is provided and can be any number of different types of coil assemblies depending upon the particular imaging device 10 and the intended application and operating modes. In the illustrated embodiment, the coil assembly 30 is in the form of a quadrature transmit/receive coil. As is well known, the coil assembly 30 has a hollow interior that is accessed through an opening 40 formed at the first end 12 of the device 10. The opening 40 is configured (shaped) to receive the animal holder 100. As described herein, the opening 40 can include a stop or locator and locking feature which ensures that the animal holder 100 is inserted into the opening 40 in a correct orientation and can serve to releasably lock the animal holder 20 in a select target location to ensure that the animal is in the correct, desired location to perform the imaging.

It will be understood that the imaging device 10 includes additional components, including electronics and control systems, that are not described in detail herein since the present invention is directed to animal holder 100 and the imaging device 10 is merely included to show one exemplary application for the animal holder 100.

FIGS. 1-5 depict the various components of the animal holder 100. The animal holder 100 has a first end 102 and an opposing second end 104 and includes a body tube 110 having a first end 112 and an opposing second end 114. The body tube 110 is configured and intended to receive a majority (e.g., a substantial portion) of the animal's body. In the case of a rodent, such as a mouse, the body tube 110 receives most of the rodent's body with the exception being the head which, as described below, is contained in a different section of the holder 100. The body tube 110 can be formed of several parts including a base portion 120 and a cover portion 130. In the illustrated embodiment, the base portion 120 has a concave shape and has semi-circular shape with curved side walls. The base portion 120 is intended to act as a floor and support the animal's body. The cover portion 130 is complementary to the base portion 120 and is designed to mate with and enclose the base portion 120 (as a result, the cover portion 130 can have a semi-circular shape). The cover portion 130 acts as a roof (ceiling) for the base portion 120 and when combined with the base portion 120, the assembled parts 120, 130 defined a tubular structure that is open at least at the first end 112 and also likely at the second end 114.

In the illustrated embodiment, the cover portion 130 is a separate part relative to the base portion 120; however, it will be appreciated that the two portions 120, 130 can be coupled to one another as by a living hinge or the like to permit the cover portion 130 to pivot open.

At the second end 114, the body tube 110 includes a member 115 for guiding the holder 100 into the opening 40 of the imaging device 10 and for positioning the holder 100 at a target location within the opening 40. The member 115 can thus represent a handle by which the holder 100 can be grasped and moved into position. The body tube 110 can also include a locking mechanism (which can be incorporated into and be a part of the coupling member 115) for releasably locking the body tube 110 within the opening 40. In one embodiment, the locating and locking mechanism can be in the form of a pin that extends downwardly from the bottom of the base portion 120 and contacts a stop/locking feature formed in the imaging device 10 within the opening 40. In other words, the opening 40 can be defined along its bottom by a guide track or the like on which the holder 100 rides until reaching the target position (where imaging occurs on the target body part (i.e., head)).

At the first end 112, the body tube 110 and in particular, the base portion 120 thereof includes a shoulder yoke assembly 140 for restraining a shoulder/neck portion of the animal that is contained within the body tube 110. The shoulder yoke assembly 140 includes a pair of slots 142, 144 formed in the side walls of the base portion 120. The slot 142 is thus formed one side of the base portion 120 and the slot 144 is formed in the other side of the base portion 120 such that the two are opposite one another, with an opening 145 being formed between the two walls structures that defines the slots 142, 144. The opening 145 receives the neck of the animal such that the head of the animal is located forward of the two slots 142, 144, while the lower body of the animal is located rearward of the two slots 142, 144.

The assembly 140 also includes a shoulder yoke 148 that is configured to fit around the shoulder/neck portion of the animal and be received and locked in place within the two slots 142, 144, to thereby secure and lock the animal's body in the desired position. The shoulder yoke 148 has a U-shape with two free ends that are inserted into the slots 142, 144. The dimensions (including thickness, etc.) of the shoulder yoke 148 are selected to produce a secure mechanical fit (friction fit) between the shoulder yoke 148 and the body tube 110. The shoulder yoke 148 thus locks into place within the body tube 110. The neck of the animal is located below the shoulder yoke 148. It will be understood that different sized yokes 148 can be used to accommodate different sized animals since the yoke 148 needs to securely fit around the neck of the animal sufficiently to prevent undesirable body movement.

The animal holder 100 also includes a head immobilization mechanism 150 that is intended, as described herein, to immobilize the head for awake brain imaging without the need for surgery, head posts, ear bars, skull pins or the use of local anesthetics. The head immobilization mechanism 150 is located at the first end 102 of the holder 100 and thus is located forward of the body tube 110. More specifically, the area immediately forward of the shoulder yoke 148 is a head receiving space 151 in which the head of the animal is received and immobilized and maintained in the desired position using mechanism 150.

Figure 4:
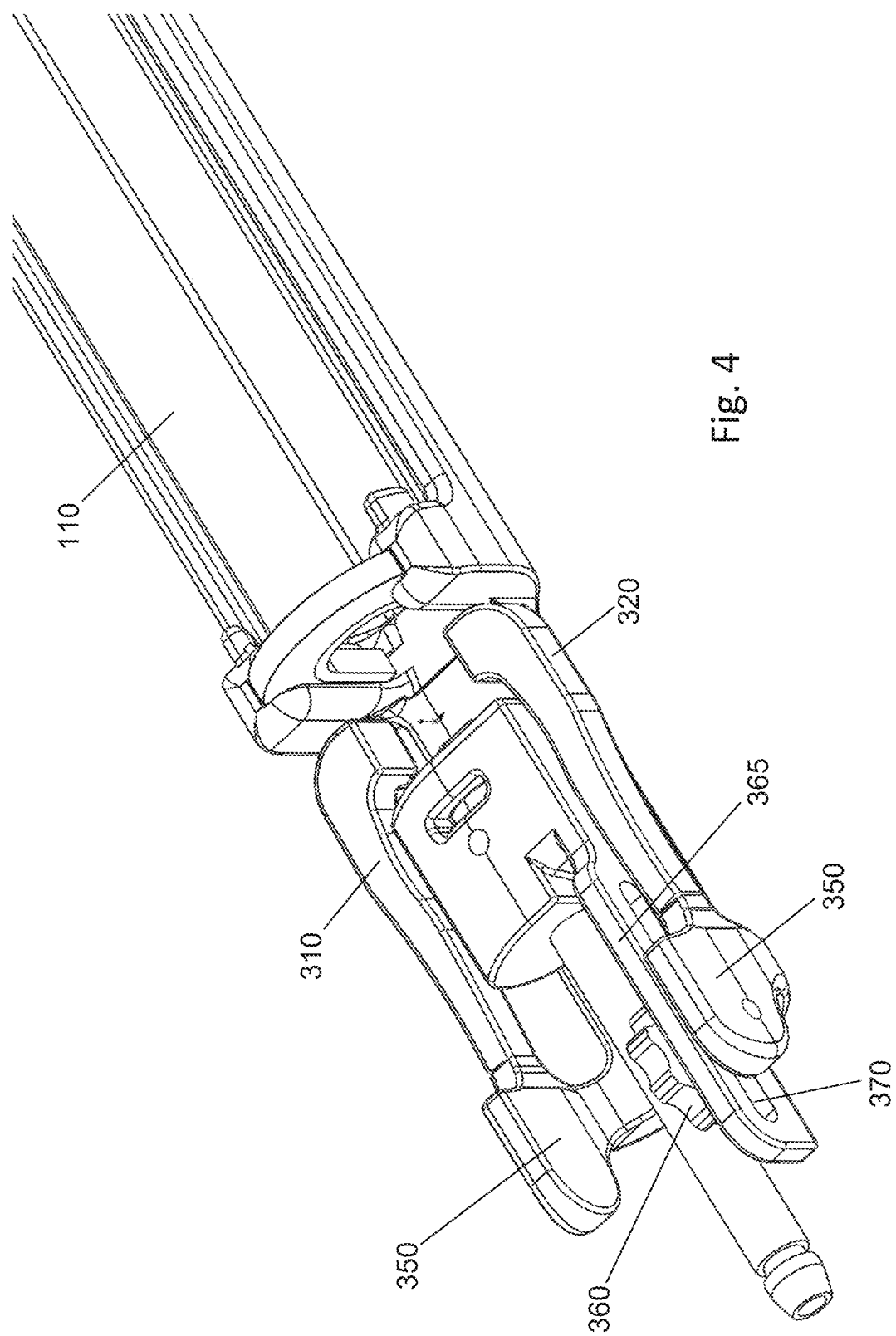
FIG. 4 is an enlarged partial side and top perspective view of the animal holder of FIG. 2 with the compressible fingers being shown in compressed positions.
Figure 5:
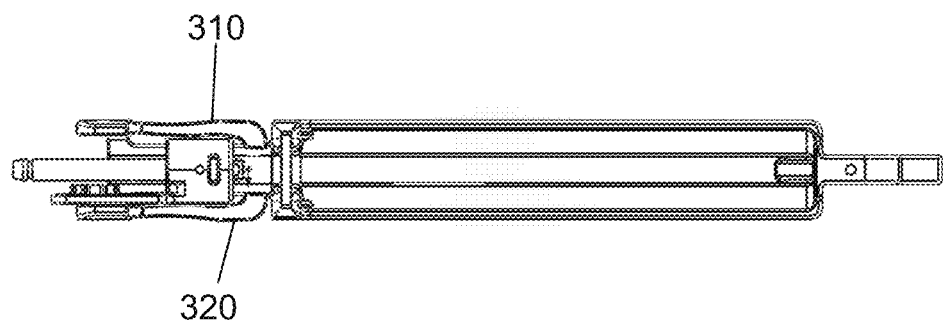
FIG. 5 is a top plan view of the animal holder of FIG. 4.

The first end 102 of the holder 100 at which the head immobilization mechanism 150 is located includes a bottom wall 300. The bottom wall 300 is preferably integrally connected to the base portion 120 of the body tube 110. The head immobilization mechanism 150 is defined by a pair of flexible (compressible) fingers 310, 320 that are connected to the bottom wall 300 but spaced therefrom and extend longitudinally along the device 100. More specifically, each of the fingers 310, 320 includes a first end 312 that is connected to the bottom wall 300 and a free second 314 that is proximate and spaced from the shoulder yoke 148. The fingers 310, 320 are flexible and can move between a first position (FIGS. 2 and 3) and a second position (FIGS. 4 and 5). The first position is a normal rest position of the fingers 310, 320 (free of an applied force), while the second position is a position in which an inwardly directed force is applied to the fingers 310, 320 to cause inward flexing thereof.

As shown in FIG. 4, the first end 312 of each respective finger 310, 320 is connected to the bottom wall 300 by a side wall 350. The two side walls 350 are thus opposite one another. The width of the device 100 at the location of the side walls 350 is at least substantially equal to the width of the device 100 at the location of the body tube 110.

The free second ends 314 can include an inwardly directed portion 315 that extends inward toward the other opposing finger.

It will be appreciated that a distance between the fingers 310, 320 is greatest when the fingers 310, 320 are in the first (rest) position and the distance between the fingers 310, 320 is less when the fingers 310, 320 are in the second (flexed) position. In particular, the fingers 310, 320 are formed such that in the first position, at least an outer portion of each finger extends beyond the side walls of the body tube 110. In other words, when the fingers 310, 320 are in the first (rest) position, the width of the device 100 is at its greatest at the location of the fingers 310, 320.

The fingers 310, 320 can carry pads, such as foam head pads, at or near the free second ends 314. The fingers 310, 320 are formed such that in the normal rest (first) position, the animal's head can easily fit between the free second ends 314 of the fingers 310, 320. The first position of the fingers 310, 320 is thus a loading position for the head of the animal. The fingers 310, 320 are constructed such that when the holder 100 is inserted into the opening 40 of the imaging device 10, the side walls of the imaging device that define the opening 40 apply a compressive (inwardly directed) force against the fingers 310, 320, thereby causing the fingers 310, 320 to flex inwardly and assume the second position (FIGS. 4 and 5) in which the width of the device 100 is the same in both the location of the fingers 310, 320 and the body tube 110. This movement is smooth since the first ends 312 of the fingers 310, 320 do not exhibit appreciable flexing and instead the distance between the ends 312 (that defines the width of the device 100 at this location) is at least substantially the same as at the body tube 110. The fingers 310, 320 are thus angled outwardly and thus, when the first end 102 of the device 100 is inserted into the opening 40 and the device 100 is continually advanced into the opening (slot) 40 of the imaging device 10, the side walls of the imaging device 10 contact and press the fingers 310, 320 inward until the fingers 310, 320 assume the second position.

The natural movement of the fingers 310, 320 from the first position to the second position, causes the inner sections 315 of the fingers 310, 320 to be drawn into contact with the head of the animal (e.g., mouse). This movement causes immobilization of the animal's head.

The animal holder 100 can also include a nose support member 200 for receiving the nose of the animal. The nose support member 200 can be in the form of a nose cone structure 210 that is located in front of the head receiving space 151. The nose support member 200 is located between the flexible fingers 310, 320 and extends longitudinally along the bottom wall. A bite plate is also preferably included and can be part of the nose support member 200. The bite plate faces the head receiving space 151 and is positioned such that it can be inserted into the mouth of the immobilized animal.

An incisor tube 210 is also provided and extends outwardly from the nose support member 200. The tube 210 serves as a connector to an odor source, such as isoflurane or stimulus odors.

As shown in FIG. 4, the nose support member 200 is locked in place using a fastener 360. The fastener 360 mates with an opening in one side wall 350 and the nose support member 200 includes an elongated extension 365 that connects a main portion of the nose support member 200. The elongated extension 365 has an elongated slot 370 formed therein. The fastener 360 includes a stem portion that is received through the slot 370 and into the opening in the side wall 350. The slot 370 permits adjustment of the nose support member 200 in the longitudinal direction by loosening the fastener 360 and adjusting the nose support member 200 in the longitudinal direction and then retightening the fastener 360.

When setting up and animal, the animal's neck is stretched by adjusting the position of nose cone (animal's mouth) relative to the shoulder yoke. This slight tension prevents the animal from using his shoulder muscles to lift his head. This feature also has the following advantage: the fastener 360 also allows the nose cone (nose support member 200) to be "flipped" out of the holder (like a folding knife). This feature allows for the user to conveniently hook the animal's mouth into the bite bar, situate the nose cone 200 and then roll the animal into the holder 100. This is much faster than the traditional method of using the bite bar/nose cone on conventional products which is rigidly fixed or only slides along the body tube.

One of the main advantages of the present holder 100 is the ease of use and the greatly reduced amount of time that is needed to load and immobilize the head of the animal prior to performing the imaging. In the present invention, the animal is simply loaded into the body tube 110 and position such that the head is in space 151 and the lower body is in the body tube 110 and then the animal is secured in place with the shoulder yoke 148. The nose cone and bite bar assembly 200 are then placed in the desired position and the holder is now in a final pre-load position. It will be noted that the head of the animal is not yet immobilized. When it is time to image the animal, the user holds the holder 100 by the handle 115 and then inserts the first end 102 of the device 100 into the opening 40. As the holder 100 is further inserted into the opening 40, the side walls of the imaging device 10 that define the opening 40 contact the fingers 310, 320 which are protruding outwardly beyond the rest of the holder 100 since they are in the first (rest) position. Continued advancement into the opening 40 results in a compressive force being applied to the fingers 310, 320 and the fingers 310, 320 flex inward until they assume the second position. As the fingers 310, 320 flex inward, the inner portions 315 of the opposing fingers 310, 320 contact the head of the animal and serve to not only position it in the desired position but also serve to immobilize the head since the head is effectively sandwiched between the two compressed fingers 310, 320. This immobilization process requires no additional steps by the user but instead is automatic and results merely by insertion of the holder 100 into the opening 40. This allows significantly more animals to be imaged per a set period of time compared to conventional holders which are manually intensive.

Once the imaging is completed, the holder 100 is grasped by the handle 115 and is pulled out of the opening 40 of the imaging device 10. Once the fingers 310, 320 clear the side walls that define the opening 40, the fingers 310, 320 naturally flex outwardly until the fingers 310, 320 assume the first (rest) position. As the fingers 310, 320 flex outwardly, the fingers 310, 320 separate from the head of the animal and thus, the animal is free to move its head. The animal can then be easily removed from the holder 100 by then removing the shoulder yoke 148 and the cover portion of the body tube 110.

It will also be understood that while the illustrated embodiment includes two fingers 310, 320, the holder 100 can be constructed so as to include a different number of fingers. For example, the holder 100 can include a single finger (e.g., finger 310) that compresses in the same manner described herein (e.g., when the holder is inserted into the opening of the imaging device, the single finger compresses. Instead of an opposing compressible finger, the holder can include a padded side wall or a fixed head rest for placement against one side of the animal's head, with the single compressible finger being in contact with the other side of the animal's head.

Figure 8:
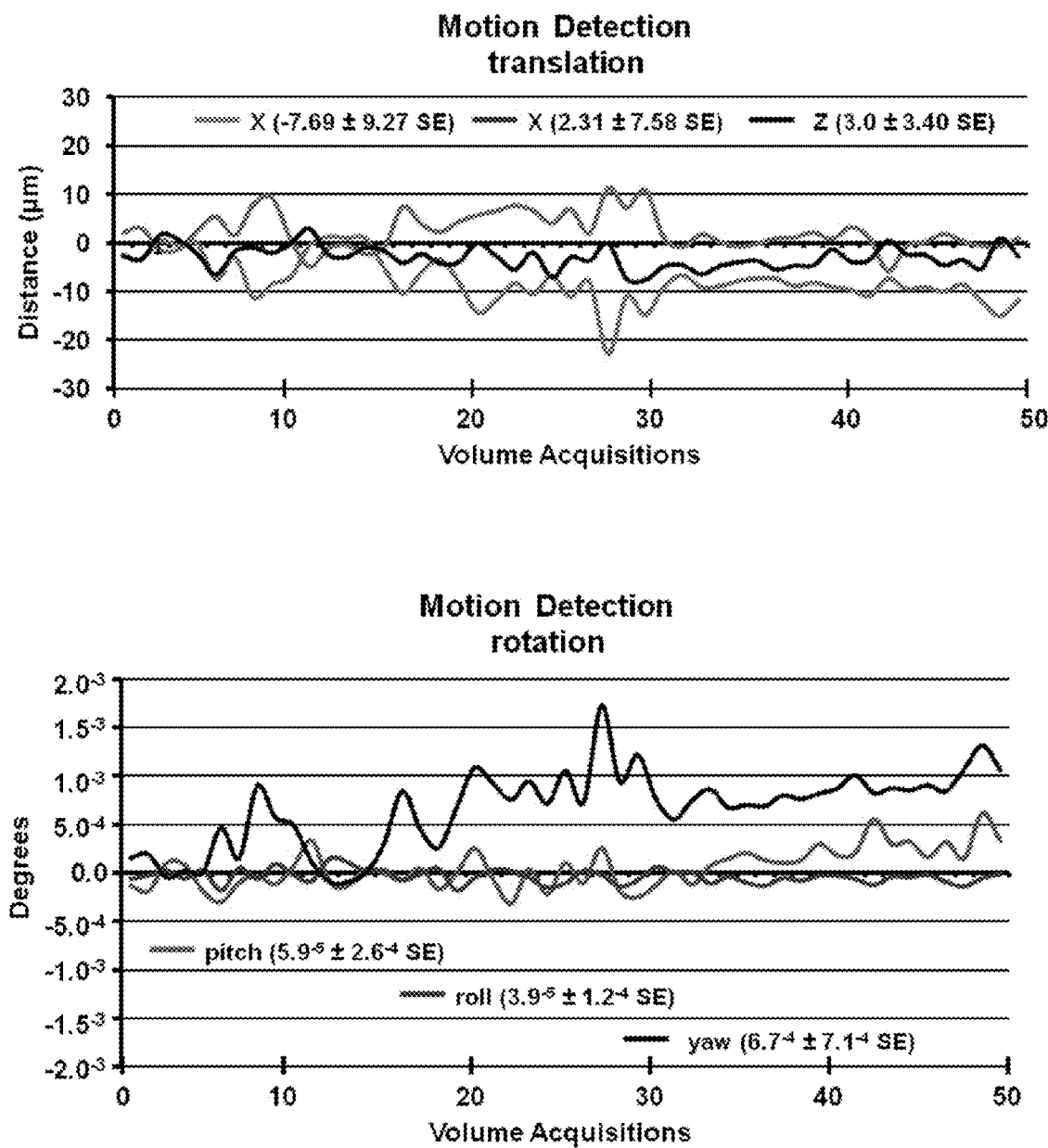
FIG. 8 contains graphs representing data obtained from motion detection software.

FIG. 8 shows results of motion detection software that shows that motion in six degrees is reduced to less than 20 microns. This data shows the advantages obtained by the present holder.

The holder 100 accommodates small rodents from 10-60 gm and thus is ideal for transgenic mice, voles and post-natal rats. In addition, with the coil stationary in the magnet, the holder 100 can be withdrawn and replaced with one another. There is no need to retune or rematch. The ease of efficiency of the holder 100 allows a significant number of more animals to be imaged per hour due to the increased speed at which the animals can be loaded and unloaded from the imaging device using the holders 100 of the present invention. In addition, the holder 100 can be used with both aware or anesthetized animals and can accommodate a heating element to allow for temperature regulation. As mentioned above, no head post, ear bars or skull pins are used and instead, head cushions are provided (as part of the flexible fingers) to minimize stress and discomfort.

While the invention has been described in connection with certain embodiments thereof, the invention is capable of being practiced in other forms and using other materials and structures. Accordingly, the invention is defined by the recitations in the claims appended hereto and equivalents thereof.

What is claimed is:

1. An animal holder for use with an imaging device comprising:
   a body tube for receiving a first body portion of the animal, the body tube having a distal end and an opposite proximal end;
   a head immobilization mechanism disposed adjacent the distal end of the body tube for receiving a head of the animal, the head immobilization mechanism including opposing first and second flexible fingers that have first ends that are fixedly attached to a structure proximate an open distal end of the head immobilization mechanism and opposite free second ends configured to contact the head of the animal, the free second ends being closer to the body tube than the first ends of the first and second flexible fingers, wherein the first and second flexible fingers move between first and second positions, wherein in the first position, at which the first and second fingers are at rest, the free second ends of the first and second fingers extend beyond an outer side wall of the body tube and define a maximum width of the holder, whereas in the second position, the free second ends of the first and second fingers are in a inwardly flexed position in which the width of the holder at a location of the free second ends of the first and second fingers is the same as the width of the body tube, whereby in the inwardly flexed position, the free second ends of the first and second fingers are configured to contact and immobilize the head of the animal; and
   a nose support member having a proximal end that faces the body tube, wherein the distal ends of the first and second flexible fingers are located distal to the proximal end of the nose support member;
   wherein the head immobilization mechanism is formed in a forward portion that is defined by a bottom wall that is connected to the distal end of the body tube and a pair of upstanding side wall portions that are integral to the bottom wall, the side walls portions being spaced apart from one another, each flexible finger comprises an elongated structure that is directly connected at the first end thereof to one of the upstanding side wall portions and extends longitudinally toward the body tube such that in the first position, a distance between the first and second flexible fingers is greatest at a location proximate the distal end of the body tube.

2. The animal holder of claim 1, wherein the body tube includes a base portion and a removable cover portion that mates with the base portion.

3. The animal holder of claim 1, wherein a distal end of the body tube includes a shoulder yoke assembly including a pair of opposing slots formed in the body tube and a U-shaped shoulder yoke that is received within the slots, wherein the U-shaped shoulder yoke is free of direct contact with the head immobilization mechanism and a center opening is formed between the slots for receiving a neck of the animal.

4. The animal holder of claim 1, wherein a width of the holder at a location of the upstanding side wall portions is the same as the width of the body tube.

5. The animal holder of claim 1, wherein in the first position, the first and second fingers flex outwardly from the upstanding side wall portions.

6. The animal holder of claim 1, wherein the free second ends of the first and second fingers include inwardly directed portions that extend inwardly toward the other opposing finger.

7. The animal holder of claim 6, wherein the inwardly directed portions include cushion pads for contacting the head of the animal.

8. The animal holder of claim 1, wherein the nose support member has a main portion for receiving a nose of the animal and an elongated extension that extends longitudinally from the main portion, the elongated extension having a slot formed therein, wherein one upstanding side wall portion to which one of the first and second flexible fingers is attached includes an opening that is axially aligned with the slot and receives a stem of a fastener passing through the slot into the opening, whereby the longitudinal slot permits adjustment of the nose support member in the longitudinal direction by loosening the fastener and moving the nose support member to another position and then tightening the fastener.

9. An animal holder for use with an imaging device comprising:
   a body tube for receiving a first body portion of the animal, the body tube having a distal end;
   a head immobilization mechanism disposed adjacent the distal end of the body tube for receiving a head of the animal, the head immobilization mechanism including first and second flexible fingers, each of which has a free proximal end configured to contact the head of the animal and an opposite distal end that is fixedly attached to a support structure, wherein the flexible finger moves between first and second positions, wherein in the first position, at which the flexible finger is at rest, the flexible finger extends beyond an outer side wall of the body tube and defines a maximum width of the holder at a location proximate the distal end of the body tube, whereas in the second position, the flexible finger is in a inwardly flexed position in which the width of the holder at a location of the free proximal end of the flexible finger is the same as the width of the body tube, whereby in the inwardly flexed position, the flexible finger is configured to contact and immobilize the head of the animal; and
   a nose support member that is located between the proximal and distal ends of each of the first and second flexible fingers;
   wherein the head immobilization mechanism is formed in a forward portion that is defined by a bottom wall that is connected to the distal end of the body tube and a pair of upstanding side wall portions that are integral to the bottom wall, the side walls portions being spaced apart from one another, each flexible finger comprises an elongated structure that is directly connected at the distal end thereof to one of the upstanding side wall portions and extends longitudinally toward the body tube such that in the first position, a distance between the first and second flexible fingers is greatest at a location proximate the distal end of the body tube.

10. The animal holder of claim 9, wherein the maximum width of the holder is at a location of the free proximal ends of the first and second flexible fingers.

11. The animal holder of claim 9, wherein the body tube includes a handle at a proximal end opposite the head immobilization mechanism.

12. An imaging system for imaging a head of a rodent comprising an imaging device having a coil that has a central opening formed therein;

an animal holder for reception within the central opening of the coil, wherein the animal holder comprises:

a body tube for receiving a first body portion of the animal;

a bottom wall extending distally from a distal end of the body tube; and a head immobilization mechanism coupled to the bottom wall and disposed adjacent the distal end of the body tube for receiving a head of the animal, the head immobilization mechanism including first and second flexible fingers, each of which has a free proximal end configured to contact the head of the animal and an opposite distal end that is fixedly attached to a wall of the bottom wall, wherein the first and second flexible fingers move between first and second positions, wherein in the first position, at which the first and second flexible fingers are at rest, the first and second flexible fingers extend beyond an outer side wall of the body tube, whereas in the second position, the first and second flexible fingers are in a inwardly flexed position in which the width of the holder at a location of the free proximal ends of the flexible fingers is the same as the width of the body tube and the first and second flexible fingers are configured to contact and immobilize the head of the animal;

wherein the first and second flexible fingers move from the first position to the second position when the animal holder is inserted into the imaging device which causes inward flexing of the free proximal ends of the first and second flexible fingers; and wherein a maximum width of the holder is greater than a maximum width of the central opening that is formed in the coil, while a width of the body tube is at least the same or less than the width of the central opening of the coil;

wherein the head immobilization mechanism is formed in a forward portion that is defined by a bottom wall that is connected to the distal end of the body tube and a pair of upstanding side wall portions that are integral to the bottom wall, the side walls portions being spaced apart from one another, each flexible finger comprises an elongated structure that is directly connected at the distal end thereof to one of the upstanding side wall portions and extends longitudinally toward the body tube such that in the first position, a distance between the first and second flexible fingers is greatest at a location proximate the distal end of the body tube.

* * * * *